(12) United States Patent
Carter et al.

(10) Patent No.: US 6,642,429 B1
(45) Date of Patent: Nov. 4, 2003

(54) PERSONAL CARE ARTICLES WITH REDUCED POLYMER FIBERS

(75) Inventors: Julia Carter, Tampa, FL (US); Darryl Franklin Clark, Alpharetta, GA (US); Bryan David Haynes, Cumming, GA (US); Matthew Boyd Lake, Alpharetta, GA (US); Caroline L. Miller, Zachary, LA (US); Kevin Edward Smith, Highlands Ranch, CO (US); Ty Jackson Stokes, Suwanee, GA (US); Jeffrey Lawrence McManus, Canton, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 72 days.

(21) Appl. No.: 09/603,278

(22) Filed: Jun. 26, 2000

Related U.S. Application Data
(60) Provisional application No. 60/141,691, filed on Jun. 30, 1999.

(51) Int. Cl.$^7$ ................................................ A61F 13/15
(52) U.S. Cl. ...................... 604/367; 604/369; 604/370
(58) Field of Search ................................ 604/367, 369, 604/370, 374, 365, 366; 428/373, 374, 393, 398

(56) References Cited

U.S. PATENT DOCUMENTS

| | | |
|---|---|---|
| 3,338,992 A | 8/1967 | Kinney |
| 3,341,394 A | 9/1967 | Kinney |
| 3,463,652 A | 8/1969 | Whitesel et al. |
| 3,502,763 A | 3/1970 | Hartmann |
| 3,542,615 A | 11/1970 | Dobo et al. |
| 3,542,909 A | 11/1970 | Breukink et al. |
| 3,549,470 A | 12/1970 | Greenwald et al. |
| 3,576,931 A | 4/1971 | Chopra et al. |
| 3,692,618 A | 9/1972 | Dorschner et al. |
| 3,802,817 A | 4/1974 | Matsuki et al. |
| 3,849,241 A | 11/1974 | Butin et al. |
| 3,855,046 A | 12/1974 | Hansen et al. |
| 3,884,030 A | 5/1975 | Baxter et al. |
| 3,969,471 A | 7/1976 | Driscoll |
| 3,969,472 A | 7/1976 | Driscoll |
| 4,020,230 A | 4/1977 | Mahoney et al. |
| 4,028,452 A | 6/1977 | Driscoll |
| 4,062,915 A | 12/1977 | Stricharczuk et al. |
| 4,085,175 A | 4/1978 | Keuchel |
| 4,104,207 A | 8/1978 | Pelikan et al. |
| 4,164,603 A | 8/1979 | Siggel et al. |

(List continued on next page.)

FOREIGN PATENT DOCUMENTS

| | | |
|---|---|---|
| DE | 2148588 | 4/1973 |
| EP | 235 051 | 9/1987 |
| EP | 338 854 | 10/1989 |

(List continued on next page.)

OTHER PUBLICATIONS

R. Beyreuther and H. Hofmann: *Melt spinning of hollow fibers*, Man–Made Fiber Year Book, 70–73, Sep. 1997.

(List continued on next page.)

*Primary Examiner*—Weilun Lo
*Assistant Examiner*—Jacqueline F Stephens
(74) *Attorney, Agent, or Firm*—Pauley Petersen & Erickson

(57) ABSTRACT

A personal care absorbent article made of a nonwoven material having a plurality of polymeric fibers having a fiber interior comprising at least one of a liquid fluid and a gaseous fluid. The nonwoven materials are produced by heating at least one polymer to a melting point, forming a molten polymer; extruding the molten polymer through a plurality of capillaries, injecting a liquid fluid and/or a gaseous fluid into the molten polymer prior to, during and/or after the extruding step, forming a plurality of fluid-filled polymeric fibers, wherein the liquid fluid and/or gaseous fluid is dispersed within the interior of the polymeric fibers, and depositing the fluid-filled polymeric fibers onto a web forming surface, forming a nonwoven material.

21 Claims, 1 Drawing Sheet

U.S. PATENT DOCUMENTS

| | | |
|---|---|---|
| 4,176,978 A | 12/1979 | Ruzicka et al. |
| 4,180,536 A | 12/1979 | Howell, Jr. et al. |
| 4,188,448 A | 2/1980 | Stricharczuk et al. |
| 4,264,670 A | 4/1981 | Kontos |
| 4,279,848 A | 7/1981 | Baxter et al. |
| 4,282,890 A | 8/1981 | Howell, Jr. et al. |
| 4,340,563 A | 7/1982 | Appel et al. |
| 4,380,594 A | 4/1983 | Siggel et al. |
| 4,401,567 A | 8/1983 | Shindo et al. |
| 4,405,688 A | 9/1983 | Lowery et al. |
| 4,483,897 A | 11/1984 | Fujimura et al. |
| 4,485,141 A | 11/1984 | Fujimura et al. |
| 4,493,629 A * | 1/1985 | Goffe .......................... 425/192 |
| 4,535,028 A | 8/1985 | Yokogi et al. |
| 4,544,594 A | 10/1985 | Li et al. |
| 4,562,022 A | 12/1985 | Li et al. |
| 4,626,390 A | 12/1986 | Li et al. |
| 4,670,341 A | 6/1987 | Lundsager |
| 4,728,472 A | 3/1988 | Windley |
| 4,753,762 A | 6/1988 | Lie et al. |
| 4,795,668 A | 1/1989 | Krueger et al. |
| 4,858,629 A | 8/1989 | Cundari |
| 4,861,661 A | 8/1989 | Samuelson |
| 5,057,368 A | 10/1991 | Largman et al. |
| 5,069,970 A | 12/1991 | Largman et al. |
| 5,108,820 A | 4/1992 | Kaneko et al. |
| 5,108,827 A | 4/1992 | Gessner |
| 5,124,197 A * | 6/1992 | Bernardin et al. .......... 428/284 |
| 5,156,905 A | 10/1992 | Bagrodia et al. |
| 5,188,625 A * | 2/1993 | Van Iten et al. ............ 604/383 |
| 5,277,976 A | 1/1994 | Hogle et al. |
| 5,336,552 A | 8/1994 | Strack et al. |
| 5,382,400 A | 1/1995 | Pike et al. |
| D356,688 S | 3/1995 | Uitenbroek et al. |
| 5,429,629 A | 7/1995 | Latimer et al. |
| 5,466,410 A | 11/1995 | Hills |
| 5,487,859 A | 1/1996 | Aneja et al. |
| 5,527,611 A | 6/1996 | Hernandez |
| 5,540,992 A | 7/1996 | Marcher et al. |
| 5,540,993 A | 7/1996 | Hernandez |
| 5,609,588 A | 3/1997 | DiPalma et al. |
| 5,620,779 A | 4/1997 | Levy et al. |
| 5,622,671 A * | 4/1997 | Pellegrin et al. ............ 264/563 |
| 5,647,883 A | 7/1997 | Houpt et al. |
| 5,989,044 A | 11/1999 | Miyamoto |
| 6,007,911 A * | 12/1999 | Bowen, Jr. .................. 428/373 |
| 6,160,199 A * | 12/2000 | Noda .......................... 604/367 |
| 6,312,545 B1 * | 11/2001 | Nickel et al. ................ 156/229 |
| 6,368,990 B1 * | 4/2002 | Jennergren et al. ......... 442/329 |

FOREIGN PATENT DOCUMENTS

| | | |
|---|---|---|
| EP | 654 492 | 5/1995 |
| GB | 1 318 964 | 5/1973 |
| JP | 68022332 | 2/1965 |
| JP | 68027551 | 7/1967 |
| JP | 70018727 | 9/1967 |
| JP | 48063025 | 9/1973 |
| JP | 49014730 | 2/1974 |
| JP | 49061414 | 6/1974 |
| JP | 50077616 | 6/1975 |
| JP | 80040682 | 2/1980 |
| NL | 6903634 | 9/1970 |
| NL | 7212859 | 3/1973 |
| WO | WO 96/00318 | 1/1996 |
| WO | 97/16585 | 5/1997 |
| WO | 98/07910 | 2/1998 |
| WO | WO 00/44411 | 8/2000 |

OTHER PUBLICATIONS

Dr. T. Harro: *New Materials Permeable to Water Vapor*, May 1999, Springer–Verlag Berlin Heidelberg New York, Berlin; Heidelberg XP002150322, p. 107–112 and p. 172–186.

Manson, John A. and Sperling, Leslie H., *Polymer Blends & Composites*, Plenum Press, a division of Plenum Publishing Corp., New York, New York, pp. 273–277 (1976).

* cited by examiner

TO DRAW UNIT

PERSONAL CARE ARTICLES WITH REDUCED POLYMER FIBERS

This application claims the benefit of Provisional application No. 60/141,691, filed Jun. 30, 1999.

FIELD OF THE INVENTION

This invention relates to personal care absorbent articles employing nonwoven web materials comprising polymeric fibers having a reduced amount of polymer compared to conventional solid polymeric fibers of corresponding dimensions. More particularly, this invention relates to polymeric fibers in which a gaseous or liquid fluid is injected into the core or center of the fibers during production of the fibers, which liquid or gaseous fluid remains in the interior of the fibers, and a method for producing such polymeric fibers. Polymeric fibers having high or low density cores and trapped liquid cores can be produced in accordance with the disclosed method. Improved characteristics of these fibers include more resilient crimp and improved insulation properties. Nonwoven web materials comprising such fibers are suitable for use in personal care absorbent articles such as diapers, incontinence garments, training pants, feminine care products such as sanitary napkins and pads, and the like.

BACKGROUND OF THE INVENTION

Nonwoven materials are defined as materials having a structure of individual fibers or threads which are interlaid, but not in a regular or identifiable manner, as in a knitted fabric. Nonwoven webs can be formed by many processes such as, for example, meltblowing processes, spunbonding processes, and bonded carded web processes. Typically, the fibers from these processes are deposited onto a forming wire or belt for formation of the web.

Nonwoven materials and laminates comprising nonwoven materials are widely used as components of absorbent articles such as disposable diapers, feminine hygiene products including sanitary pads and tampons, incontinence garments, disposable medical garments and the like, and much effort has been made to improve the effectiveness and functionality of these articles. These articles generally include a liquid absorbent material backed by a liquid-impervious barrier sheet. To enhance the sense of comfort, the absorbent material has a facing of a material which masks at least the body-facing surface of the product. The purpose of this cover or liner material is to help structurally contain the absorbent material and to protect the wearer from continuous direct contact with moisture from previously wetted absorbent material. The cover material is typically a relatively low basis weight nonwoven fabric. Improved product performance has been obtained in these products through the incorporation of a surge management material disposed between this cover material and the absorbent material. (See U.S. Pat. No. 5,429,629.) The surge management material is made from a relatively high basis weight, low density, that is thick, nonwoven web material. The cover material must, therefore, be permeable to liquids on the side of the product that is placed against the body, actively promoting the immediate transfer of each liquid application or insult through the surge management material and into the absorbent pad. It is also necessary that the surge management material initially hold the liquid passed through the cover material and then give up said liquid to the absorbent material.

One characteristic of a liner material which affects the fluid intake characteristics of the material is the amount of void volume within the material. In particular, by increasing the amount of void volume, the fluid intake characteristics, that is the ability of the liner material to initiate fluid intake, is improved. For nonwoven liners, void volume, or pore size, is typically increased by increasing the fiber diameter which, in turn, translates into a higher amount of polymer per unit length of fibers making up the liner material. However, increasing the fiber diameter of solid fibers by conventional means results in an increase in the amount of polymer required to produce the fibers which make up the liner material.

In addition to the benefits derived from increasing the fiber diameter as discussed hereinabove, there are also benefits derived from increasing the surface area of the fibers comprising a nonwoven web material. For example, increasing the surface area of the fibers enables the application of a greater amount of topical surfactant to the fibers, which, in turn, may also enhance the fluid uptake ability of the nonwoven web. To increase the surface area of a solid fiber by conventional means, it is typically necessary, as in the case of increasing fiber diameter, to increase the polymer amount per unit length of fiber.

SUMMARY OF THE INVENTION

Accordingly, it is one object of this invention to provide a nonwoven material having fibers with a reduced polymer weight per unit length of fiber compared to conventionally formed solid fibers having corresponding dimensions.

It is another object of this invention to provide a personal care absorbent article employing such nonwoven materials.

It is another object of this invention to provide a method for increasing the dimensional characteristics, such as fiber diameter and surface area, of a polymeric fiber suitable for use in nonwoven materials without increasing the amount of polymer utilized per unit length of fiber.

It is another object of this invention to provide a method for increasing the dimensional characteristics, such as fiber diameter and surface area, of a polymeric fiber suitable for use in nonwoven materials while decreasing the amount of polymer utilized per unit length of fiber compared to fibers produced by conventional means having corresponding dimensional characteristics.

It is yet another object of this invention to provide nonwoven materials having improved, more resilient crimp and improved insulation properties over conventional nonwoven materials.

These and other objects are addressed by a personal care absorbent article comprising a nonwoven material comprising a plurality of polymeric fibers having a fiber interior comprising at least one of a liquid fluid and a gaseous fluid. In accordance with one embodiment of this invention, the gaseous and/or liquid fluid is dispersed, for example as a plurality of tiny bubbles, throughout at least a portion of the fiber interior. The polymeric fibers may be spunbond fibers, meltblown fibers, bicomponent fibers, biconstituent fibers, bonded carded fibers and combinations thereof. In accordance with one embodiment of this invention, at least a portion of the polymeric fibers are crimped. Personal care absorbent articles in which these fibers may be used include, but are not limited to, disposable diapers, incontinence garments, training pants, feminine care products including sanitary pads and tampons, wipes, surgical gowns and wound dressings.

Polymeric fibers for use in nonwoven materials for personal care absorbent articles in accordance with this invention are produced by a method comprising the steps of introducing at least one polymer suitable for forming polymeric fibers into an extruder and heating said polymer to an extrusion temperature, forming a molten polymer, introducing a blowing agent in the form of a liquid and/or gaseous fluid into the molten polymer, and extruding the polymer, resulting in the formation of a plurality of polymeric fibers having a reduced amount of polymer per unit of length of fiber compared to conventional solid polymeric fibers having corresponding fiber dimensional characteristics. In accordance with one embodiment of this invention, the blowing agent is introduced into the at least one polymer prior to extrusion, resulting in the blowing agent being dispersed within at least a portion of the extruded polymeric fibers. In accordance with one embodiment of this invention, the extruded polymeric fibers are monocomponent or bicomponent fibers wherein the blowing agent is introduced substantially only into one of the polymer streams forming the extruded bicomponent fibers. For example, for a bicomponent fiber having a sheath-core configuration, the blowing agent may be disposed substantially only in the core portion of the bicomponent fiber. Alternatively, each component of the bicomponent fiber may include a different blowing agent dispersed throughout the component. In accordance with yet a further embodiment of this invention, the polymeric fibers are biconstituent fibers wherein the blowing agent is dispersed within one polymeric component of the biconstituent fibers.

It will be apparent to those skilled in the art that the polymeric fibers of this invention, while not necessarily having a reduced weight per unit of fiber volume or length (the weight being a function in part of the blowing agent employed), will, nevertheless, have a reduced amount of polymer per unit of volume compared to polymeric fibers of comparable dimensions without any blowing agent. This is due to the displacement of a portion of the otherwise polymeric volume of the fibers by the blowing agent.

It also will be apparent to those skilled in the art that the type of blowing agent(s) used as well as the manner in which it is introduced into the fiber will impact the end product fiber characteristics. Thus, the type of blowing agent employed may be predicated upon imparting a particular characteristic to the fibers to satisfy the requirements of the personal care absorbent article in which it is used. A center-filled fiber can be produced having high or low density cores, liquid trapped cores, improved, more resilient crimp and improved insulation properties. This, in turn, will affect the properties of nonwoven materials produced using these fibers, such as basis weight, void volume, etc. Suitable blowing agents are gaseous or liquid fluids which are unreactive with the fiber polymer. Gaseous fluids, such as high pressure air and nitrogen, are preferred.

BRIEF DESCRIPTION OF THE DRAWINGS

These and other objects and features of this invention will be better understood from the following detailed description taken in conjunction with the drawings wherein.

DEFINITIONS

Figure 1A:
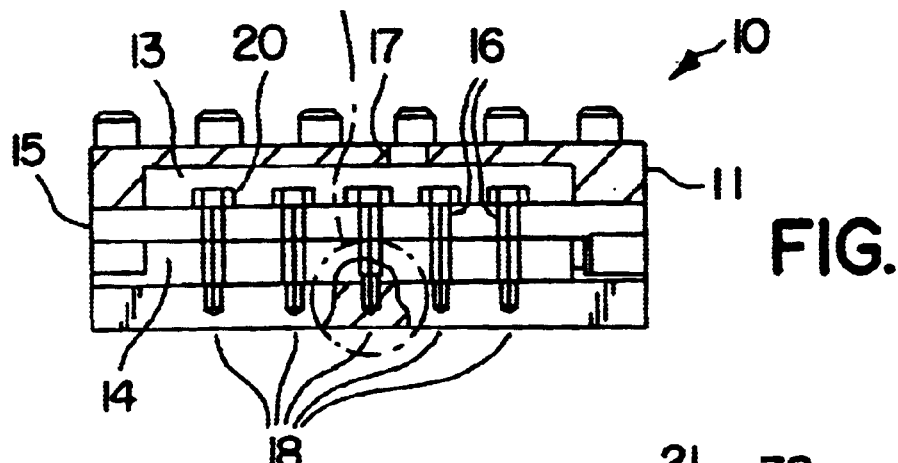
FIG. 1A is a cross-sectional view of a portion of a spinplate suitable for producing the fluid-filled fibers of this invention.

As used herein, the term "nonwoven web" or "nonwoven material" means a material having a structure of individual fibers or threads which are interlaid, but not in an identifiable manner, as in a knitted fabric. Nonwoven materials or webs have been formed from many processes such as, for example, spunbonding processes, meltblowing processes, and bonded carded web processes. The basis weight of nonwoven fabrics is usually expressed in grams per square meter (gsm) and the fiber diameters are usually expressed in microns.

As used herein, the term "spunbond fibers" refers to small diameter fibers which are formed by extruding molten thermoplastic material as filaments from a plurality of fine, usually circular capillaries of a spinneret, with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. No. 3,338,992 and 3,341,394 to Kinney, U.S. Pat. No. 3,502,763 to Hartmann, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 50 microns. The fibers may also have shapes such as those described in U.S. Pat. No. 5,277,976 to Hogle et al., U.S. Pat. No. 5,466,410 to Hills, and U.S. Pat. No. 5,069,970 and U.S. Pat. No. 5,057,368 to Largman et al., which describe hybrids with unconventional shapes. A nonwoven web of spunbond fibers produced by melt spinning is referred to as a "spunbond".

As used herein, the term "meltblown fibers" means fibers formed by extruding a molten thermoplastic material through a plurality of fine, usually circular, die capillaries as molten threads or filaments into converging high velocity, usually hot, gas (for example, air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, by U.S. Pat. No. 3,849,241 to Butin et al. Meltblown fibers are microfibers which may be continuous or discontinuous, are generally smaller than 10 microns in average diameter, and are generally tacky when deposited onto a collecting surface.

As used herein, the term "microfibers" refers to small diameter fibers having an average diameter not greater than about 75 microns, for example, having an average diameter of from about 0.5 microns to about 50 microns, or more particularly, having an average diameter of from about 2 microns to about 40 microns. Another frequently used expression of fiber diameter is denier, which is defined as grams per 9000 meters of a fiber, and may be calculated as fiber diameter in microns squared, multiplied by the density in grams/cc, multiplied by 0.00707. A lower denier indicates a finer fiber and a higher denier indicates a thicker or heavier fiber. For example, a diameter of a polypropylene fiber given as 15 microns may be converted to denier by squaring, multiplying the results by 0.89 g/cc and multiplying by 0.00707. Thus, a 15 micron polypropylene fiber has a denier of about 1.42. Outside the United States, the unit of measurement is more commonly the "tex", which is defined as the grams per kilometer of fiber. Tex may be calculated as denier/9.

As used herein, the term "polymer" generally includes, but is not limited to, homopolymers, copolymers, such as for example, block, graft, random and alternating copolymers, terpolymers, etc., and blends and modifications thereof In addition, unless otherwise specifically limited, the term "polymer" also includes all possible geometric configurations of the molecule. These configurations include, but are not limited to, isotactic, atactic, syndiotactic and random symmetries.

As used herein, the term "monocomponent" fiber refers to a fiber formed from one or more extruders using only one polymer. This is not meant to exclude fibers formed from one polymer to which small amounts of additives have been added for coloration, anti-static properties, lubrication, hydrophilicity, etc. These additives, for example titanium dioxide for coloration, are generally present in an amount less than about 5 weight percent and more typically about 2 weight percent.

As used herein, the term "bicomponent fibers" refers to fibers which have been formed from at least two different polymers extruded from separate extruders but spun together to form one fiber. Bicomponent fibers are also sometimes referred to as conjugate fibers or multicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement. Bicomponent fibers are taught by U.S. Pat. No. 5,108,820 to Kaneko et al., U.S. Pat. No. 4,795,668 to Krueger, et al., U.S. Pat. No. 5,540,992 to Marcher et al., and U.S. Pat. No. 5,336,552 to Strack et al. Bicomponent fibers are also taught by U.S. Pat. No. 5,382,400 to Pike et al., and may be used to produce crimp in the fibers by using the differential rates of expansion and contraction of the two (or more) polymers. For two component fibers, the polymers are desirably present in ratios of 75/25 to 25/75 or any other desired ratio and, as an example, may be 50/50.

As used herein, the term "biconstituent fibers" refers to fibers which have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils which start and end at random. Biconstituent fibers are sometimes also referred to as multiconstituent fibers. Fibers of this general type are discussed in, for example, U.S. Pat. No. 5,108,827 to Gessner. Bicomponent and biconstituent fibers are also discussed in the textbook Polymer Blends and Composites by John A. Manson and Leslie H. Sperling, copyright 1976 by Plenum Press, a division of Plenum Publishing Corporation, New York, N.Y. IBSN 0-306-30831-2, at pages 273 through 277.

As used herein, the term "spin pack" refers to an apparatus for producing multiconstituent fibers having fiber configurations such as sheath-core, multi-lobal, pie and side-by-side configuration fibers. Suitable spin packs for use in the method of this invention are taught by U.S. Pat. No. 5,162,074 and related U.S. Pat. No. 5,466,410, both to Hills, as well as U.S. Pat. No. 5,989,044 to Cook.

As used herein, "thermal point bonding" involves passing a fabric or web of fibers to be bonded between a heated calender roll and an anvil roll. The calender roll is usually, though not always, patterned in some way so that the entire fabric is not bonded across its entire surface. As a result, various patterns for calender rolls have been developed for functional as well as aesthetic reasons. Typically, the percent bonding area varies from around 5% to around 30% of the area of the fabric laminate web. As is well known in the art, the spot bonding holds the laminate layers together as well as imparts integrity to each individual layer by bonding filaments and/or fibers within each layer. Exemplary bond patterns are taught by U.S. Pat. No. 3,855,046 to Hansen et al., U.S. Pat. No. 5,620,779 to Levy et al., and U.S. Pat. No. 356,688 to Uitenbroek et al., all of which are incorporated herein by reference.

As used herein, "through-air bonding" ("TAB") is a process of bonding a nonwoven bicomponent fiber web in which air sufficiently hot to melt one of the polymers in the fibers of the web is forced through the web. The air velocity is between 100 and 500 feet per minute and the dwell time may be as long as 6 seconds. The melting and resolidification of the polymer provides the bonding. TAB has relatively restricted variability and since TAB requires the melting of at least one component to accomplish bonding, it is most effective when applied to webs with two components like conjugate fibers or those which include an adhesive. In the through-air bonder, air having a temperature above the melting temperature of one component and below the melting temperature of another component is directed from a surrounding hood, through the web, and into a perforated roller supporting the web. Alternatively, the through-air bonder may be a flat arrangement wherein the air is directed vertically downward onto the web. The operating conditions of the two configurations are similar, the primary difference being the geometry of the web during bonding. The hot air melts the lower melting polymer component and thereby forms bonds between the filaments to integrate the web.

DESCRIPTION OF PREFERRED EMBODIMENTS

The physical characteristics of polymeric fibers used in the nonwoven materials of this invention are altered to impart one or more desired characteristics to the nonwoven materials in accordance with the method of this invention by injecting the polymeric fibers during production with a gaseous and/or liquid fluid (blowing agent). For example, the density of the nonwoven materials may be increased or decreased depending upon the density of the gaseous or liquid fluids employed. In addition, for a polymeric fiber of a given dimension, such as outside diameter, the amount of polymer required to produce the polymeric fiber is reduced when compared to corresponding polymeric fibers which have not been injected with a gaseous or liquid fluid due to displacement of the polymer by the gaseous or liquid fluid within the fibers.

Depending upon the property or characteristic desired to be imparted to the polymeric fibers and, in turn, the nonwoven materials comprising such polymeric fibers, it may be desirable to distribute the blowing agent substantially uniformly throughout the fibers or localized within a portion of the fibers. In the former case, the blowing agent is preferably injected into the molten polymer prior to formation of the fibers whereas, in the latter case, the blowing agent is preferably injected into the fibers after formation such as by extrusion, although it will be apparent that, in the case of multicomponent fibers, the blowing agent may be injected into one of the polymers comprising the multicomponent fibers prior to extrusion so as to localize the blowing agent within the one polymer. Suitable blowing agents are any gaseous fluids such as air, nitrogen, helium, etc. or liquid fluids such as oils, which are unreactive with the polymer used to produce the fiber.

Fibers utilized in the nonwoven materials of this invention preferably are selected from the group consisting of spunbond fibers, meltblown fibers, bicomponent fibers, biconstituent fibers, carded staple fibers, and combinations thereof. In addition, the fibers utilized in the nonwoven materials of this invention may have any fiber shape.

Suitable polymers for use in accordance with this invention are selected from the group consisting of polyolefins, polyamides, polyesters, polycarbonates, polystyrenes, thermoplastic elastomers, fluoropolymers, vinyl polymers, and blends and copolymers thereof. Suitable polyolefins include, but are not limited to, polyethylene, polypropylene, polybutylene, and the like; suitable polyamides include, but are not limited to, nylon 6, nylon 6/6, nylon 10, nylon 12 and the like; and suitable polyesters include, but are not limited to, polyethylene terephthalate, polybutylene terephthalate and the like. Particularly suitable polymers for use in the present invention are polyolefins including polyethylene, for example, linear low density polyethylene, low density polyethylene, medium polyethylene, high density polyethylene and blends thereof; polypropylene; polybutylene and copolymers as well as blends thereof. Additionally, the suitable fiber forming polymers may have thermoplastic elastomers blended therein. Of these suitable polymers, particularly suitable polymers to the structural component of suitable conjugate fibers include polypropylene and copolymers of polypropylene and ethylene, and particularly suitable polymers for the adhesive component of the conjugate fibers include polyethylenes, more particularly linear low density polyethylene, and high density polyethylene.

Figure 2:
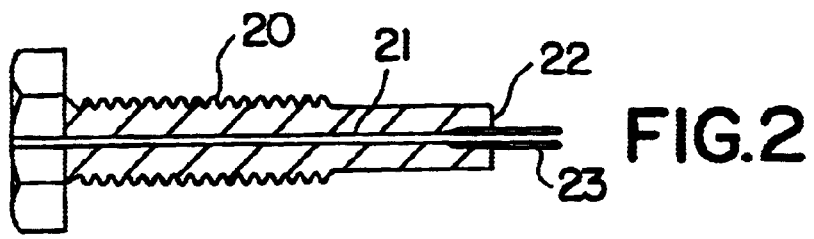
FIG. 2 is a diagram showing detail of the bolts utilized in the spinplate of FIG. 1 for injection of the liquid or gaseous fluid into the polymeric fibers of this invention.

FIG. 1A shows a portion of a spinplate 10 suitable for use in the production of fluid-filled polymeric fibers in accordance with this invention. The spinplate 10 comprises at least one wall 11 enclosing a chamber which is divided into an injection fluid plenum 13 and a polymer chamber 14 by intermediate wall 15, which at least one wall forms an opening 17 for introduction of an injection fluid into injection fluid plenum 13. Intermediate wall 15 forms a plurality of openings 16 in which are disposed means for conveying the injection fluid or blowing agent through the molten polymer but without contact with the molten polymer disposed in polymer chamber 14 to the capillary exits 18 of the spinplate. In accordance with one embodiment, the means for conveying the injection fluid through the polymer chamber to each capillary exit comprises a bolt 20, shown in detail in FIG. 2, which forms a fluid conduit 21 within the core of the bolt which fluid conduit 21 extends the entire length of the bolt 20. Fitted into the injection fluid outlet end 22 of the fluid conduit 21 is a length of microtubing 23 through which the injection fluid is injected into the interior of the extruded polymeric fiber.

Figure 1B:
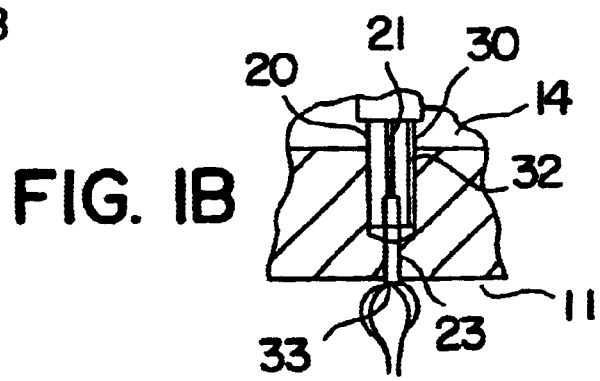
FIG. 1B is a cross-sectional view of a capillary exit of one of the capillaries comprising the spinplate of FIG. 1A.

FIG. 1B is a partial cross-sectional view of a capillary exit suitable for use in injecting a gaseous or liquid fluid into the interior of an extruded fiber. As shown, the at least one wall 11 which is disposed toward the bottom of polymer chamber 14 forms an opening 30 into which the injection fluid outlet end 22 of the fluid conduit 21 extends. Opening 30 is sized to accommodate injection fluid outlet end 22 and microtubing 23 extending therefrom so as to form an annular region 32 between the outer surface of the injection fluid outlet end 22 of fluid conduit 21 and the wall of opening 30 and between the outer surface of microtubing 23 and the wall of opening 30 which, in the area surrounding microtubing 23, has a reduced diameter compared to the portion of opening 30 surrounding injection fluid outlet end 22 of fluid conduit 22. Annular region 32 provides fluid communication between polymer chamber 14 and the capillary exit 33, enabling molten polymer to flow from polymer chamber 14 through capillary exit 33. Simultaneous with the extrusion of polymer, the desired gaseous and/or liquid fluid, flowing through fluid conduit 21 and microtubing 23, is injected into the interior of the polymer passing through the capillary. From there, in the case of spunbond fibers, the resulting fiber is passed to a draw unit (not shown) for further reduction in outside diameter. Using the apparatus of FIGS. 1A, 1B and 2, it is possible to obtain fibers where the injected fluid fills 70% or more of the core of the fibers. It will also be appreciated by those skilled in the art that, in order for the fibers to retain the injected fluid in the interior of the fibers, the fibers are not porous.

Figure 3:
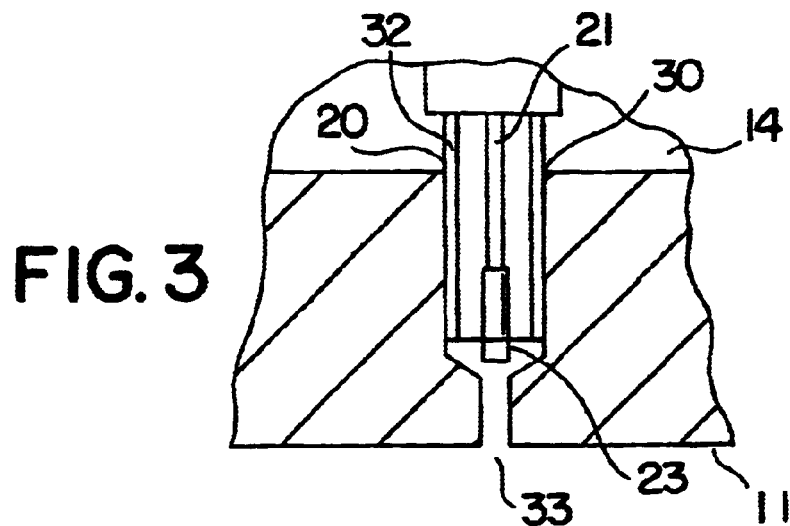
FIG. 3 is a cross-sectional view of a capillary exit of a spinplate suitable for producing fluid-containing fibers in accordance with one embodiment of this invention.

FIG. 3 is a partial cross-sectional view of a capillary exit suitable for use in dispersing a gaseous and/or liquid fluid throughout at least a portion of the interior of polymeric fibers used in the nonwoven web material of this invention. In contrast to the capillary of FIG. 1B in which the lower end of microtubing 23 extends past the capillary exit 33, the lower end of microtubing 23 is disposed upstream of the final capillary, thereby enabling the gaseous and/or liquid fluid to be injected into the polymer prior to extrusion.

It will also be appreciated by the artisan that the injection fluid may be injected into the polymer in a number of ways to produce a desired affect. For example, in accordance with one embodiment of this invention, the injection fluid is introduced slightly off center to provide some twist or crimp to the fiber. In addition, two or more polymers can be used to produce a multicomponent fiber to provide more crimp, or such a multicomponent fiber may be produced from incompatible resins such that splitting occurs. With the reduced amount of polymer used to produce the fibers of this invention, polymers with higher viscosities than typical spunbond resins may be able to be drawn down to desirable levels, providing better material properties, such as improved tensile strength.

Nonwoven materials comprising the fluid-filled polymeric fibers in accordance with this invention may often need to be bonded in order to provide integrity to the web, and optionally further bonded to provide added strength, depending upon the application. For nonwoven materials comprising polypropylene fibers, thermal point bonding is preferred. Nonwoven materials employing bicomponent fibers in accordance with this invention may be bonded either by thermal point bonding or through-air bonding.

The method of this invention is also suitable for producing foam-like structures for spunbond, bicomponent spunbond and meltblown fibers. In accordance with this embodiment of the invention, foam-like filled fibers are produced by utilizing a gaseous fluid such as nitrogen or high pressure air as the core component of a sheath core pack. The gaseous fluid is introduced into the polymer upstream of the final capillary in the spin plate near the exit of the capillary in the spin plate, creating bubbles in the center of the fiber. The fiber is then drawn down in a conventional draw unit, producing a foam-like filled fiber. Core density is controlled by controlling the amount of gaseous fluid introduced. Fibers having a foam-like core structure have many advantages including reduced raw material usage, finer fibers due to the low density core, the enhancement of fiber splitting due to the reduction in surface area, and improved high rate spinning due to faster quenching and improved insulation properties due to the entrapped bubbles.

By way of example, a control sheath/core bicomponent fiber was produced having a sheath/core diameter of 20.73 microns (PP) which equals about 2.7 denier. A fluid-filled fiber produced in accordance with the method of this invention was created by injection at 20 psig with 1% by volume blowing agent into the core of a PP/PP sheath/core fiber resulting in a fiber having a diameter of about 24.27 microns which corresponds to the diameter of a 3.7 denier PP fiber. As can be seen, the effective denier increase was 37%. Fibers such as those produced in accordance with the method of this invention having increased diameters have improved resiliency, loft, capillary dimensions, and surface area.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A personal care absorbent article comprising:
a nonwoven material comprising a plurality of polymeric fibers comprising at least one of a liquid fluid and a gaseous fluid dispersed throughout at least a portion of an interior of said polymeric fibers, said at least one of the liquid fluid and the gaseous fluid filling greater than 70% of said interior, wherein said polymeric fibers comprise at least one polymer selected from the group consisting of polyolefins, polyamides, polyesters, polycarbonates, polystyrenes, thermoplastic elastomers, fluoropolymers, vinyl polymers, and blends and copolymers thereof.

2. A personal care absorbent article in accordance with claim 1, wherein said polymeric fibers are selected from the group consisting of spunbond fibers, meltblown fibers, bicomponent fibers, biconstituent fibers, bonded carded fibers, and combinations thereof.

3. A personal care absorbent article in accordance with claim 1, wherein at least a portion of said polymeric fibers are crimped.

4. A personal care absorbent article in accordance with claim 1, wherein said at least one of said liquid fluid and said gaseous fluid are substantially uniformly dispersed throughout said interior of said polymeric fibers.

5. A personal care absorbent article in accordance with claim 1, wherein said at least one of said liquid fluid and said gaseous fluid are localized within a portion of said interior of said polymeric fibers.

6. A personal care absorbent article in accordance with claim 1, wherein said nonwoven material is a laminate.

7. A personal care absorbent article in accordance with claim 1, wherein at least a portion of said plurality of polymeric fibers are bicomponent fibers wherein said at least one of said liquid fluid and said gaseous fluid are disposed substantially all within a core component of said bicomponent fibers.

8. A personal care absorbent article comprising:
a nonwoven material comprising a plurality of polymeric fibers comprising at least one of a liquid fluid and a gaseous fluid dispersed throughout at least a portion of an interior of said polymeric fibers, said at least one of the liquid fluid and the gaseous fluid filling greater than 70% of said interior, wherein at least a portion of said plurality of polymeric fibers are biconstituent fibers wherein said at least one of said liquid fluid and said gaseous fluid are disposed substantially all within one polymer comprising said biconstituent fibers.

9. A nonwoven material comprising:
a nonwoven web comprising a plurality of polymeric fibers comprising at least one of a liquid fluid and a gaseous fluid dispersed throughout at least a portion of an interior of said polymeric fibers, said at least one of the liquid fluid and the gaseous fluid filling greater than 70% of said interior, wherein said polymeric fibers comprise at least one polymer selected from the group consisting of polyolefins, polyamides, polyesters, polycarbonates, polystyrenes, thermoplastic elastomers, fluoropolymers, vinyl polymers, and blends and copolymers thereof.

10. A nonwoven material in accordance with claim 9, wherein said polymeric fibers are selected from the group consisting of spunbond fibers, meltblown fibers, bicomponent fibers, biconstituent fibers, bonded carded fibers, and combinations thereof.

11. A nonwoven material in accordance with claim 9, wherein at least a portion of said fibers are crimped.

12. A nonwoven material in accordance with claim 9, wherein said at least one of said liquid fluid and said gaseous fluid are substantially uniformly dispersed throughout said interior of said polymeric fibers.

13. A nonwoven material in accordance with claim 9, wherein said at least one of said liquid fluid and said gaseous fluid are localized within a portion of said interior of said polymeric fibers.

14. A nonwoven material in accordance with claim 9 further comprising a plurality of nonwoven layers.

15. A nonwoven material comprising:
a nonwoven web comprising a plurality of polymeric fibers comprising at least one of a liquid fluid and a gaseous fluid dispersed throughout at least a portion of an interior of said polymeric fibers, said at least one of the liquid fluid and the gaseous fluid filling greater than 70% of said interior, wherein at least a portion of said plurality of polymeric fibers are biconstituent fibers wherein said at least one of said liquid fluid and said gaseous fluid are disposed substantially all within one polymer comprising said biconstituent fibers.

16. A nonwoven material in accordance with claim 15, wherein at least a portion of said plurality of polymeric fibers are bicomponent fibers wherein said at least one of said liquid fluid and said gaseous fluid are disposed substantially all within a core component of said bicomponent fibers.

17. A disposable diaper comprising:
at least one nonwoven material comprising a plurality of polymeric fibers comprising at least one of a liquid fluid and a gaseous fluid dispersed throughout at least a portion of an interior of said polymeric fibers, said at least one of the liquid fluid and the gaseous fluid filling greater than 70% of said interior, wherein said polymeric fibers comprise at least one polymer selected from the group consisting of polyolefins, polyamides, polyesters, polycarbonates, polystyrenes, thermoplastic elastomers, fluoropolymers, vinyl polymers, and blends and copolymers thereof.

18. A feminine hygiene product comprising:
at least one nonwoven material comprising a plurality of polymeric fibers comprising at least one of a liquid fluid and a gaseous fluid dispersed throughout at least a portion of an interior of said polymeric fibers, said at least one of the liquid fluid and the gaseous fluid filling greater than 70% of said interior, wherein said polymeric fibers comprise at least one polymer selected from the group consisting of polyolefins, polyamides, polyesters, polycarbonates, polystyrenes, thermoplastic elastomers, fluoropolymers, vinyl polymers, and blends and copolymers thereof.

19. A wound dressing comprising:

at least one nonwoven material comprising a plurality of polymeric fibers comprising at least one of a liquid fluid and a gaseous fluid dispersed throughout at least a portion of an interior of said polymeric fibers, said at least one of the liquid fluid and the gaseous fluid filling greater than 70% of said interior, wherein said polymeric fibers comprise at least one polymer selected from the group consisting of polyolefins, polyamides, polyesters, polycarbonates, polystyrenes, thermoplastic elastomers, fluoropolymers, vinyl polymers, and blends and copolymers thereof.

20. A nonwoven material comprising:

a nonwoven web comprising a plurality of polymeric fibers having a fiber interior comprising at least one of a liquid fluid and a gaseous fluid, said at least one of the liquid fluid and the gaseous fluid filling greater than 70% of said fiber interior, wherein at least a portion of said fibers are meltblown fibers.

21. A personal care absorbent article comprising:

a nonwoven material comprising a plurality of polymeric fibers comprising at least one of a liquid fluid and a gaseous fluid dispersed throughout at least a portion of an interior of said polymeric fibers, said at least one of the liquid fluid and the gaseous fluid filling greater than 70% of said interior, wherein said polymeric fibers are selected from the group consisting of spunbond fibers, meltblown fibers, bicomponent fibers, biconstituent fibers, and combinations thereof.

* * * * *